United States Patent [19]

Ballay et al.

[11] Patent Number: 5,789,247
[45] Date of Patent: Aug. 4, 1998

[54] EXPRESSION IN NON-TUMORAL HUMAN LYMPHOBLASTOID LINES WITH AN INTEGRATIVE VECTOR

[76] Inventors: Annick Ballay, 3 rue la Pérouse, 78150 Le Chesnay; Georges Boffa, 62 Chemin de Vauhallan, F-92120 Palaiseau; Jean-Pierre Cartron, 2 square Robiac, F-75007 Paris; Stany Chretien, 18 rue Gramme; Patrick Lambin, 54 rue des Entrepreneurs, both of F-75015 Paris; Claude Lopez, 39 avenue Georges Clemenceau, F-94360 Bry-Sur-Marne; Sylvie Prigent, 9 bis rue du Royaume, F-91440 Bures-Sur-Yvette; Charles Salmon, 12 rue Fabre d'Eglantine, F-75012 Paris, all of France

[21] Appl. No.: 321,613

[22] Filed: Oct. 12, 1994

(Under 37 CFR 1.47)

Related U.S. Application Data

[63] Continuation of Ser. No. 190,074, Apr. 1, 1994, abandoned.
[51] Int. Cl.⁶ .............. C12N 5/22; C12N 15/63; C07H 21/04; C12P 21/06
[52] U.S. Cl. ............. 435/372.2; 435/69.1; 435/320.1; 536/23.1; 536/24.1
[58] Field of Search .................. 435/69.1, 240.2, 435/320.1, 372.2; 536/23.1, 24.1

[56] References Cited

PUBLICATIONS

C. Svensson et al., Proc. Natl. Acad. Sci. USA, Vo. 83, pp. 4690–4694, 1986.
M. Levrero et al., Gene. vol. 101, No. 2, pp. 195–202, 1991.
3–Biochem. Genetics. vol. 103: 48859j, p. 117, 1985.
3–biochem. Genetics. vol. 103: 136210w, p. 205, 1985.
M. Okamoto et al., Biotechnology, 1990, pp. 650–653.
R. C. Mulligan et al., Proc. Natl. Acad. Sci. USA vol. 78, No. 4, pp. 2072–2076, 1981.
H. Yanagi et al., Gene. vol. 76, pp. 19–26, 1989.
Sambrook et al. Integration of viral DNA sequences in cells transformed by adenovirus 2 Or SV40. Proceedings of the Royal Society of London, Series B. 210:423–435, Nov. 1980.
Berkner, K.L. Expression of heterologous sequences in adenoviral vectors. Current Topics in Microbiology and Immunology. 158:39–60, 1992.
Yang et al., 1986, Cell, 47:3–10.

*Primary Examiner*—Douglas W. Robinson
*Assistant Examiner*—Thanda Wai
*Attorney, Agent, or Firm*—Birch, Stewart, Kolasch & Birch, LLP

[57] ABSTRACT

A plasmid vector designed for transforming lymphoblastoid cells, immortalized by Epstein Barr virus, for producing heterologous proteins, which comprises the bacterial DNA elements required for its amplification together with the following DNA fragments:

the DNA elements which constitute an expression cassette allowing the insertion of a heterologous DNA to be expressed in the human lymphoblastoid cells, the Adenovirus 5 derived DNA sequence encoding the VA I and VA II RNA aimed at optimizing the messenger RNA translation, a gene engineered to be efficient as a selective marker in eukaryotic cells, and DNA segments selected for their property to promote plasmid DNA integration into the cell chromosome DNA.

14 Claims, 2 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:

( A ) LENGTH: 35 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO:1:

AGCTTGCGGC CGCGGTTACC AGATCTACGC GTGTT    35

( 2 ) INFORMATION FOR SEQ ID NO:2:

( i ) SEQUENCE CHARACTERISTICS:
            ( A ) LENGTH: 30 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO:2:

ACGCCGGCGC CAATGGTCTA GATGCGCCAA    30

( 2 ) INFORMATION FOR SEQ ID NO:3:

( i ) SEQUENCE CHARACTERISTICS:
            ( A ) LENGTH: 30 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO:3:

CGTGATATTC TCGGCCTCCT TGGCCTCCAA    30

( 2 ) INFORMATION FOR SEQ ID NO:4:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO:4:

CTGGAGTGTC CATGGGACAG    20

( 2 ) INFORMATION FOR SEQ ID NO:5:

( i ) SEQUENCE CHARACTERISTICS:
            ( A ) LENGTH: 18 base pairs
            ( B ) TYPE: nucleic acid
            ( C ) STRANDEDNESS: double
            ( D ) TOPOLOGY: linear ( i i ) MOLECULE TYPE: other nucleic acid ( x i ) SEQUENCE DESCRIPTION: SEQ ID NO:5:

AGGCGGGAGA TGGGGTGC    18

( 2 ) INFORMATION FOR SEQ ID NO:6:

( i ) SEQUENCE CHARACTERISTICS:
            ( A ) LENGTH: 30 base pairs
            ( B ) TYPE: nucleic acid
            ( C ) STRANDEDNESS: double
            ( D ) TOPOLOGY: linear -continued (ii) MOLECULE TYPE: other nucleic acid (xi) SEQUENCE DESCRIPTION: SEQ ID NO:6:

TAAGTGTGTT ATAATTTCAT CGATCATGTT    30

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: double
        (D) TOPOLOGY: linear     (ii) MOLECULE TYPE: other nucleic acid     (xi) SEQUENCE DESCRIPTION: SEQ ID NO:7:

GATCCAAACA TGAGCCGCCT    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: double
        (D) TOPOLOGY: linear     (ii) MOLECULE TYPE: other nucleic acid     (xi) SEQUENCE DESCRIPTION: SEQ ID NO:8:

ATGTCCCGAG GCGCTGTGGT    20

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: double
        (D) TOPOLOGY: linear     (ii) MOLECULE TYPE: other nucleic acid     (xi) SEQUENCE DESCRIPTION: SEQ ID NO:9:

TTGCTCTAAG CACTTGAGCA GGAAGCTCTG    30

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: double
        (D) TOPOLOGY: linear     (ii) MOLECULE TYPE: other nucleic acid     (xi) SEQUENCE DESCRIPTION: SEQ ID NO:10:

CACAGAGAGA AAGGCTAAAG    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: double
        (D) TOPOLOGY: linear     (ii) MOLECULE TYPE: other nucleic acid -continued ( x i ) SEQUENCE DESCRIPTION: SEQ ID NO:11:

ATTCCCATTC TTCTGCCATG                    20

EXPRESSION IN NON-TUMORAL HUMAN LYMPHOBLASTOID LINES WITH AN INTEGRATIVE VECTOR

This application is a continuation of application Ser. No. 08/190,074, filed on Feb. 1, 1994, now abandoned.

FIELD OF THE INVENTION

The present invention relates to the use of human cell lines for producing heterologous proteins, particularly therapeutically useful proteins, on an industrial scale, after genetic engineering of their coding sequence.

SUMMARY OF THE INVENTION

More precisely, the invention relates to the use of human lymphoblastoid cell lines, which have been immortalized in vitro by Epstein-Barr virus (EBV) and selected for their absence of tumoral or tumorigenic character. In order to ensure the expression of heterologous proteins by said cells, the protein coding sequence is inserted into a genetically engineered vector plasmid, of the integrative-type and bearing an expression cassette designed to promote the expression of said proteins in the transformed lymphoblastoid cells after cloning and selection for the integration of said expression cassette into the cell chromosome DNA.

The invention is also directed to the design and the construction of said vector plasmid aimed at promoting an optimal expression of heterologous proteins by the transformed lymphoblastoid cells.

BACKGROUND OF THE INVENTION

Production of therapeutically useful proteins which are hard to purify from natural sources where they are present in very small amounts or from potentially dangerous sources like tumors or blood plasma possibly contaminated with viruses, still justifies investments in research and development on in vitro cell cultures, under well standardized conditions and with total safety guarantee.

The expression of large size molecules whose biological activity is dependent of their structure and correct maturation (glycosylation, sialylation . . . ) is not possible in any kind of cell, and in particular it is not possible in microorganisms which are easy to grow in industrial scale fermentors. On the contrary in eukaryotic cells the maturation process is efficient but the cell culture, by itself, is not obvious on an industrial scale because most non tumoral cells only grow as monolayers, thus attached to the culture vial. Significant improvements result from the use of micro-carriers for culture in bioreactors but some cell types do not adapt to these supports; moreover this culture method is inappropriate when the proteins are not excreted in the culture medium. On the other hand some cell types very suitable for this kind of culture, like the Vero cell line, are hardly transformed by genetic engineering.

Investigations leading to new cell lines and suitable vectors allowing genetic engineering of said cells are still worth the efforts.

The Applicants have thus envisaged the use of human lymphoblastoid cell lines similar to those already used for the production of monoclonal antibodies but such a use involves the design of suitable cloning and expression vectors specially adapted for these cells.

A human lymphoblastoid line, known as Namalva, has already been used to produce a heterologous protein; this cell line grows in suspension and secretes the heterologous protein in the culture medium wherefrom it can be harvested, still in a biologically active form (Yanagi et al. Gene 1989, 76,19 et DNA 1989,8,419), but this cell line derives from a Burkitt lymphoma and is highly tumorigenic.

DETAILED DESCRIPTION OF THE INVENTION

It is one purpose of the present invention to make use of human lymphoblastoid cell lines which are non-tumoral and non-tumorigenic.

This kind of cells are already known it is possible to immortalize blood B lymphocytes from a healthy donor by transformation with EBV (Epstein-Barr virus) and to select those cell lines that do not synthesize the nucleic antigen EBNA-1 of EBV (Thoda et al. Cancer Res. 38, 1978, 3560). Such cell lines grow indefinitely in culture but are not tumoral, as confirmed by their absence of colony-forming capacity in-agar medium and their absence of tumorigenicity in nude mice (Gurtsevitch et al. Int J. Cancer 47, 87, 1988, Turszz, Medecine/Sciences 6, Suppl.42, 1989).

The Applicants are already using this kind of cell lines for producing monoclonal antibodies. They have designed a suitable culture medium with low protein content in order to facilitate the purification process of secreted proteins (French patent 2 600 076).

This cell-type has already been used as a model for the expression of heterologous proteins of which the coding gene has been inserted into an autonomous replicon which remains as an episome in the cell because it bears the EBV origin of replication which is under the control of the EBNA-1 protein of the EBV used to immortalize the cell line (Kioussis et al. EMBO J.6, 1987, 355; Young et al. Gene 62, 1988, 171; Jalanko et al. Gene 78, 1989, 287).

Nevertheless the episomal state of this replicon does not guarantee the stability of its cellular copy-number and thus its capacity to produce the heterologous protein as a function of time, above all on an industrial scale which implies a very large number of cell multiplication cycles.

It is thus another aspect of the present invention to design, by genetic engineering, a vector which includes all the elements required for the expression of a heterologous protein in the human lymphoblastoid cells as well as DNA sequences which promote integration of the whole construction into the chromosome DNA of the host cell.

In one aspect, therefore, the invention is directed to the use of human lymphoblastoid cell lines, being in vitro immortalized with EBV and selected for their absence of tumoral or tumorigenic character, said cells being either derived from the B lymphocytes of a randomly selected healthy donor or, among such cell lines, the one chosen and well characterized, and deposited at the ATCC with the accession number CCL 156 RPMI 1788.

The use, according to the present invention, is suitable for the production, on an industrial scale, of heterologous proteins encoded by a fragment of DNA designed to be inserted into a genetically engineered vector plasmid, of the integrative-type and bearing an expression cassette which includes all the elements allowing the expression of said heterologous proteins once the expression cassette is integrated into the chromosome DNA of the lymphoblastoid cells.

In another aspect, the invention is directed to the design and engineering of the vector plasmid suitable for the use of the lymphoblastoid cells for the production of heterologous proteins. Said plasmid includes besides the bacterial DNA elements necessary of its amplification in a host like *E.coli* which derive from the starting pMLP10 plasmid (Ballay et al. Hepadna Viruses, 1987, 481 Ed. Alan R. Liss), the elements which constitute an expression cassette allowing the insertion of any heterologous DNA to be expressed in the human lymphoblastoid cells;

the Adenovirus 5 derived DNA sequence encoding the VA I and VA II RNA aimed at optimizing the messenger RNA translation (Mathews, Cell 6, 223, 1975; Soderland et al, Cell 7, 585, 1976; Schneider et al, Cell 37, 291, 1984, Svensson et al. EMBO J. 4, 957, 1985);

a gene engineered to be efficient as a selective marker in eukaryotic cells: one may choose the *E. coli* DNA coding for xanthine-guanine-phosphoribosyl-transferase (XGPRT) inserted under the control of Herpes simplex 1 (HSV1) TK gene promotor and maturation signals (Mulligan Berg. Proc. Natl. Acad. Sci. USA 98, 2072, 1981); one may also use the mouse dihydrofolate reductase cDNA (DHFR) which allows gene amplification in the presence of methotrexate (Alt et al, J. Biol. Chem. 253, 1357, 1978); one may also make use of both selection genes, inserted at different locations in the vector plasmid;

DNA segments selected for their property to promote plasmid DNA integration in the chromosome DNA of the lymphoblastoid cell. These elements will preferably be chosen among the mouse mitochondrial DNA segments known to promote tandem multimerization of heterologous DNA during the integration process into the genome of mammalian cells (Lutfalla et al. Somatic cell and Mol. Genetics, 11, 223, 1985).

The expression cassette comprises a series of elements forming a transcription unit which is functional in the chosen cells, and more precisely it comprises:

upstream of the position where the heterologous DNA will be inserted, a set of regulatory elements derived from human adenoviruses and including an activator sequence, a promotor and a leader sequence;

and downstream of this position, a polyadenylation signal derived from the virus SV40.

The elements derived from the human adenoviruses are preferably:

the Adenovirus 5 promoter (Lavery et al. J. Virol. 61, 14666, 1987) put under the control of a transcription activator sequence, upstream of the promotor, preferably the E1A activator sequence of Adenovirus 5, the major late promotor (MLP) of Adenovirus 2 coupled with one copy of cDNA of the tripartite leader sequence of Adenovirus 2 which insures a more efficient translation of messenger RNAs.

Those various independent elements are described by Berkner (Biotechniques 6, 616, 1988).

The choice is not restricted to those elements; other elements derived from adenoviruses may also be used such as the major late promotor of Adenovirus 5 and the enhancers of BKV (Grinnell et al, Mol Cell. Biol. 6, 3596–3605, 1986) or SV40 (Zenke et al, EMBO J. 5, 387–397, 1986) or more precisely their tandem association (Berg et al., Nucl. Acid. Res. 16, 1635, 1988).

The central zone of the expression cassette aimed at integrating the heterologous DNA sequence has been designed to provide rare restriction sites in order to facilitate the integration process, said restriction sites being Not I, Bst E II, Bgl II, Mlu I.

The invention is more particularly directed to the use of the cells together with the plasmid as described before, in order to produce therapeutically useful proteins which are hard to purify from natural sources. Thus, in one aspect, the invention is directed to the insertion of DNA sequences coding for the heterologous proteins into the expression cassette as described before. The vector plasmid is then introduced into the cells by electroporation (Potter et al. Proc. Natl. Acad. Sci. USA 81, 7161, 1984).

The human erythropoietin DNA was used as a first model to demonstrate the technical feasibility of the protein production as described. The erythropoietin will be called hereafter "Epo" or "RH Epo" (for recombinant human Epo). It is also possible to use a DNA coding for a similar protein with erythropoietin activity.

The natural Epo protein is synthesized in the kidneys and circulates in very small amounts in the plasma. It plays a major role in the maturation process of erythrocytes.

It contains 166 aminoacids and between 40 and 50% of carbohydrates which restricts the choice of host cells suitable for its synthesis. Its purification from urine of aplasic patients (Mikake et al. J. Biol. Chem. 252 5558, 1977) and kidney tumors (Sherwood et al. Endocrinology 99, 504, 1976) has been described but cannot be extrapolated on an industrial scale.

The production of recombinant human Epo in various cell types (COS, CHO, BHK, NIH 3T3) has also been published but the drawbacks of these cells have been discussed before.

A second model has been tested with the coding sequence of Interleukin-3 (IL-3).

IL-3 is a glycoprotein of 20–26 KDa which promotes proliferation and differentiation of hematopoietic stem cells giving rise to erythrocytes, megakaryocytes, granulo-macrophages, eosinophils and basophils, and of which human CDNA has been cloned by Yang et al. (Cell 47, 3–10, 1986). In mice, IL-3 is involved in the self-regeneration and differentiation of the multipotent stem cell CFU-S, in synergy with IL-1. Moreover IL-3, in synergy with cell-line specific cytokines, promotes growth and activity of mature cells (such as macrophages, mastocytes, neutrophil and basophil polynuclear cells). The involvement of IL-3 in the stimulation of hematopoietic stem cells could find a therapeutical application in the treatment of marrow-aplasia (Shrader, Ann. Rev. Immunol. 4, 205–230, 1986; Mizel, FASEB J. 3, 2379, 1989; Tigaud et al., medecine/sciences 7, 444, 1991). IL-3 has also been shown to stimulate hematopoiesis in primates, in synergy with GM-CSF (Donahue et al., Science 241, 1820, 1988).

A third model has been tested with the coding sequence of GM-CSF (granulocyte-macrophage colony stimulating factor). GM-CSF is also a multi-protein, i.e. a growth factor which, like IL-3, promotes growth and differenciation of various hematopoietic cell lines (lines of granulo monocytes, erythrocytes and mixed colonies) and activity of mature cells (macrophages).

The human gene of GM-CSF has been cloned by various teams (Wong et al, Science 228, 810, 1985; Lee et al, Proc. Natl Acad; Sci. USA 82, 4360, 1985; Cantrell et al, Proc. Natl Acad; Sci USA 82, 6250, 1985; Miyatake et al, EMBO J. 4, 2561, 1985) and this molecule is presently evaluated in clinical studies on human beings for treating marrow aplasia, viral (EBV, HIV) leucopenia and cytopenia induced by anti-neoplasic chemotherapy (Clark et Kamen, Science 236, 1229, 1987; Groopman et al, N. Engl. J. Med. 321, 1449, 1989; Applebaum et al, Sem. Hematol. 26, 7, 1989; Solal-Céligny, medecine/Sciences 4, 231, 1991; Tigaud et al., medecine/sciences 7, 444, 1991).

In other aspects, the present invention is also directed to the transformed cell lines after stable integration of a vector plasmid, as described before, which have been selected, by screening of numerous transformed clones, for their high yield of secretion of the desired heterologous protein.

The harvesting and purification procedures are determined according to each protein characteristics.

BRIEF DESCRIPTION OF THE DRAWINGS

E: activator sequence of E1A Gene of Ad5
MLP: major late promotor of Ad2
L: cDNA of the tripartite leader sequence of Ad2
CAT: bacterial gene coding for chloramphenicol acetyl transferase
L1: polylinker from pUC18
L2: synthetic oligonucleotide
P: coding sequence of the heterologous protein
pA: polyadenylation signal from SV40
XGPRT: bacterial gene coding for xanthine-guanine-phosphoribosyl transferase.
VA: Ad5 genes coding for the VA RNAs
mito: mouse mitochondrial DNA segment
DHFR: mouse cDNA coding for dihydrofolate reductase.

FIG. 2 shows the structure of the integrative-type expression vector pTS 39.
mito-DNA: mouse mitochondrial DNA segment.
A second selective marker (DHFR) is inserted in a bicistronic position upstream to the P sequence.

The following examples are intended to illustrate the invention without limiting its scope.

EXAMPLE 1
Construction of the Integrative Vector

Figure 1:
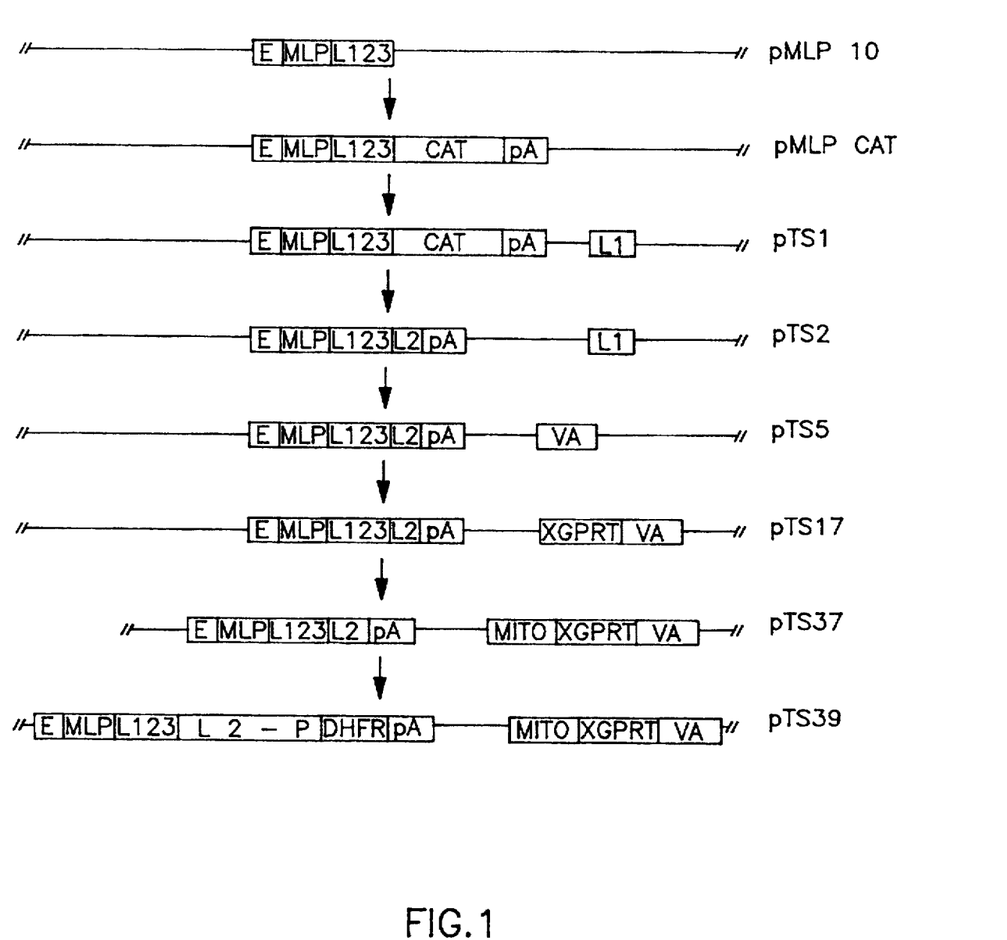
FIG. 1 shows the construction of vector plasmid pTS39. All constructions are derived from the plasmid pMLP10. The following abbreviations are used for the various DNA segments.
Figure 2:
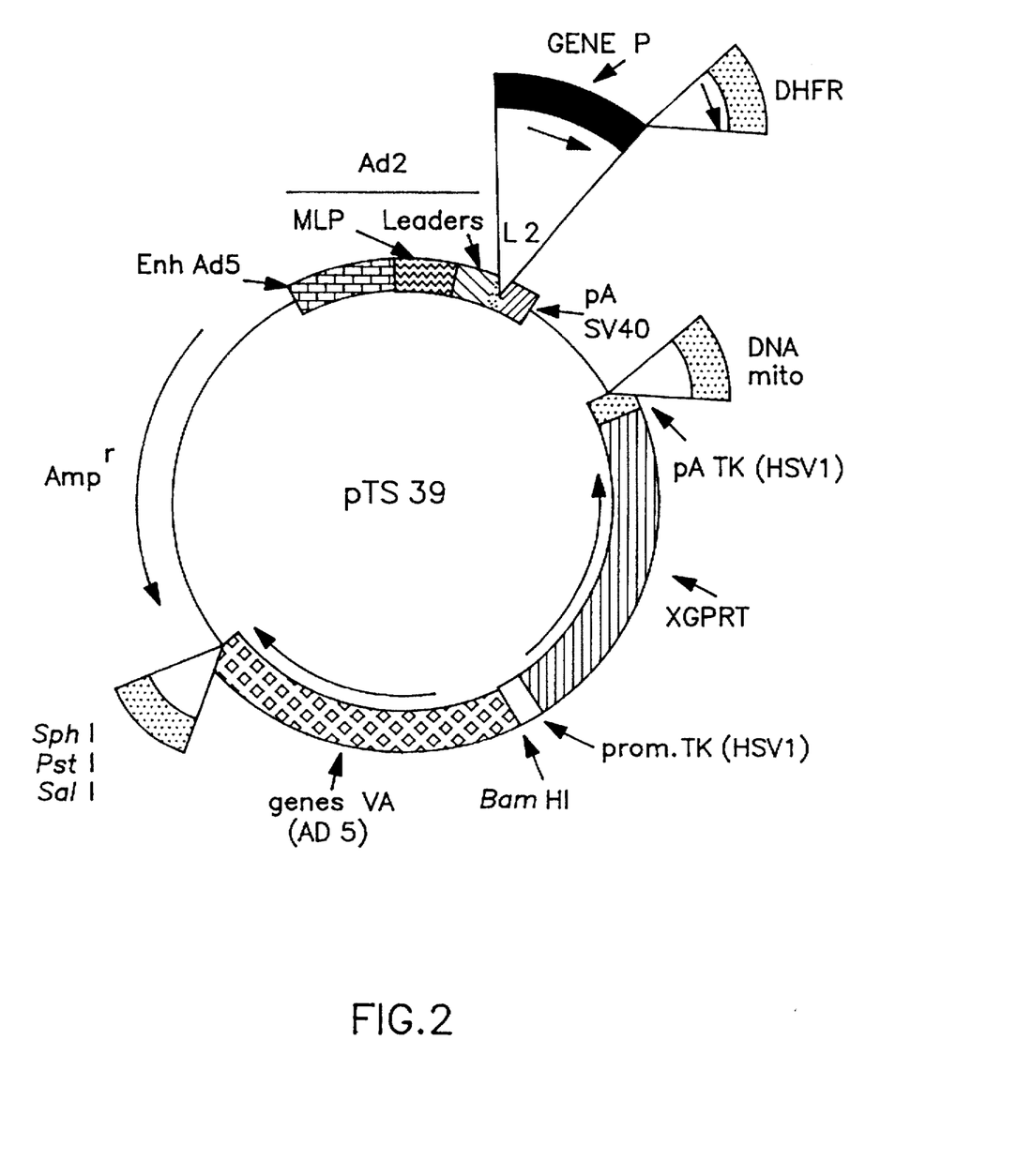

The integrative vector pTS39 shown on FIG. 2 was made by the following steps, as shown on FIG. 1:

The starting plasmid is pMLP10 (Ballay et al. Hepadna Viruses, 481, 1987, Ed. Alan R. Liss).

pMLPCAT results from the insertion into pMLP10 of the Hind III-Bam HI fragment from pHp34-CAT which bears the CAT gene and maturation signals from SV40 (P. Gilardi et al, Nucleic Acid Research 20. 7877–7887, 1984), between the Hind III and Bam HI sites of pMLP10.

Plasmid pTS1 results from the insertion of the polylinker Eco RI-HindIII from pUC18 into the NruI site of pMLP-CAT.

Plasmid pTS2 results from the insertion into pTS1 of the following synthetic nucleotide (called L2 in the figure)

AGCTTGCGGCCGCGGTTACCAGATCTACGCGTG
TT-3' (SEQ ID NO:1)
ACGCCGGCGCCAATGGTCTAGATGCGCACAA-5'
(SEQ ID NO:2)

which includes the rare restriction sites NotI, SacII, BstEII, BglII, MluI between the HindIII-HpaI sites of pTS1, and wherein the coding sequence of the desired heterologous protein (P) will be inserted.

Plasmid pTS5 results from the insertion of the Hind III fragment of pAG60VA (which bears the VAI and VAII genes of Ad5) into the XbaI site of pTS2.

Plasmid pTS17 results from the insertion of the PvuII fragment from pAGT40 (which bears the XGPRT gene under the control of the promotor and maturation signals of the HSV1 Tk gene), into the Sma I site of pTS5.

Plasmid pTS37 results from the insertion of the EcoRI-PvuI fragment from p81 which bears the mouse mitochondrial DNA sequence, into the ScI site of pTS17.

Plasmid pTS39 results from the insertion of the BamH1-BglII fragment from pTG1086 (which bears the coding sequence of the mouse DHFR cDNA, i.e., an alternative selective marker instead of XGPRT) into the Bgl II site of pTS37, so that it is positioned as a bicistron in front of the P coding sequence inserted into the L2 oligonucleotide.

Plasmid pTS39 will be called pTS39-P when a heterologous protein coding sequence will be inserted into the L2 oligonucleotide (thus called L2-P).

EXAMPLE 2
Use of plasmid pTS39 for the production of human erythropoietin in human lymphoblastoid cells. 2.1 Isolation of the Epo aene A genomic DNA library was screened with a 30-mer oligonucleotide: 
5'-CGTGATATTCTCGGCCTCCTTGGCCTCCAA-3' (SEQ ID NO:3) which was deduced from the sequence of the gene (as published by Lin et al, Proc. Natl. Acad. Sci; USA 82, 7580, 1985). This probe is complementary to the reverse of the mRNA and identifies the positions 129–159 in the sequence of Epo (base n° 1 corresponding to the initiation of translation).

EMBL3 was used as cloning vector. Human DNA fragments of 12–20 Kb are inserted into this vector. $10^7$ clones were inoculated onto 10 dishes (15 cm diameter); 3 series of blots of these dishes were washed and hybridized with the oligonucleotide probes, labeled with T4 polynucleotide kinase to a specific activity of $10^9$ cpm/µg, in the following conditions:

pre-hybridization: 3×SSC, 2×Denhardt's medium, 0.005% tetrasodium diphosphate (Nappi), 100 µg/ml salmon sperm, at 52° C. for 4 hours.

hybridization: 6×SSC, 2×Denhardt's medium, 0.05% Nappi, 20 µg/ml t.RNA, at 55° C. overnight in the presence of the Epo probe ($10^6$ cpm/ml per filter).

washing: −2×SSC, at room temperature −2×SSC, 0.005% Nappi, at 52° C., 3 times for 20 minutes further washing: 1×SSC, 0.05% Nappi at 52° C. for 20 minutes and/or 0.1×SSC, 0.05% Nappi at 52° C. for 20 minutes Four successive screenings were performed and resulted in the characterization of 3 pure clones which strongly hybridize with the probe.

The DNA of these 3 phages was amplified and analyzed. In order to confirm the presence of the complete Epo gene, the restriction map of the 3 clones was established and the presence of the 3' and 5' ends of the Epo gene was checked with oligonucleotide probes hybridizing with both ends. Two out of three clones were shown to bear the complete Epo gene.

Restriction fragments bearing the complete Epo gene were subcloned in an amplification vector like pUC. Two such fragments were subcloned: a BanHI-HindIII fragment of 5.4 Kb and a BglII-BglII fragment of 4Kb.

2.2 Isolation of the human Epo cDNA

Total RNAs were isolated from a kidney tumor which constitutively expresses Epo. From these total RNAs, the polyA RNA fraction was isolated through a oligo-dT column and cloned using the PCR technique.

Two probes surrounding the Epo cDNA were chosen
INTS 10: 5'-CTGGAGTGTCCATGGGACAG-3' (SEQ ID NO:4) This 20-mer oligonucleotide is at position 694 from Adenosine 1 of ATG (start of translation of the Epo mRNA). This oligonucleotide matches with the reverse of the complementary sequence of Epo mRNA and borders the 3' end of the cDNA.

INTS 9: 5'-AGGCGGGAGATGGGGTGC-3' (SEQ ID NO:5) This 20-mer oligonucleotide has the same orientation as the mRNA and borders the 5' end of the Epo cDNA (at position 10 from the A1 of the start codon).

The INTS 10 probe is useful for reverse transcription of the Epo MRNA template. After transcription, the MRNA is degraded in the presence of soda for 1 hour at 65° C. The single stranded cDNA is then amplified by PCR technique using the 2 probes INTS10 and INTS9 surrounding the cDNA. As a result, a 723bp DNA fragment was amplified and isolated by electrophoresis, cloned in a pUC-type amplification vector and sequenced.

2.3 Insertion of the Epo coding sequences into pTS39 vector

The Epo coding sequence (genomic or cDNA) was inserted into the L2 oligonucleotide of plasmid pTS39 as a BstEII-BglII fragment between the Hind III and Bgl II sites.

The resulting constructions are called pTS39-Epo.

2.4 Cell transfection and selection of transformed cells

Transfection was performed with an electroporation apparatus (ATEIM$^R$-Bioblock-France).

Prior to transfection, 2 aqueous solutions were prepared:
the fusion medium: Inositol 250 mM, KH$_2$PO$_4$ 1 mM, Mg Acetate 0.5 mM, Ca Acetate 0.1 mM, pH 7.4.
the post-fusion medium: NaCl 132 mM, KCl 8 mM, KH$_2$PO$_4$ 1 mM, Mg Acetate 0.1 mM, Ca Acetate 0.1 mM, pH 7.4.

Cells were grown for 2 days and then washed and adjusted to 4 10$^7$/ml in the fusion medium. The cell suspension was incubated for 10 min at 0° C. in the presence of 5 µg DNA/10$^6$ cells. A sample of the suspension was placed between the electrodes of the apparatus and electroporation was performed under the following conditions: 4 rectangular impulses at 1 second intervals for 100 µS, with an electric field of 1500 V/cm$^2$. Directly after the electric choc, the suspension was diluted 1/20 and incubated for 20 min. at 37° C. Cell viability was evaluated between 20 and 60%. Afterwards cells were cultivated at a 0.5 10$^6$ cells/ml concentration.

48 hours after transfection an aliquot of supernatant was taken for Epo dosage. The cells were further cultivated in selective medium (ISCOVE®, 10% dialyzed calf serum, mycophenolic acid 1 µg/ml, xanthine 250 µg/ml) which corresponds to the selection gene XGPRT.

2.5 Production of HR-Epo with the transformed cells *
ATCC-CCL156 cells transformed with the expression vector pTS 39-Epo.

About 6 10$^6$ CCL156 cells were transfected by electroporation with 30 µg plasmid DNA and 48 hours later cultivated in the presence of selective medium containing xanthine and mycophenolic acid. The surviving resistant cells were cloned by limiting dilution in the presence of feeder cells (irradiated human lymphocytes). Among the various clones obtained, one clone, n° 156 0.5 AF8, secretes about 100–150 units of Epo per ml of culture medium in 72 hours. It was followed in the presence and absence of selective pressure. This clone was found to be stable for 48 passages, i.e. about 7 months in the absence of selective pressure.

Southern blot analysis of total DNA extracted from clone 156 0.5 AF8 indicated that the vector pTS39-Epo is integrated as a tandem in the cellular genome and that 15 to 20 copies are present in each cell, whether cultivated in the presence or in the absence of selective pressure.

In roller culture, clone 156 0.5 AF8 secretes 80 to 100 U Epo/ml after 3 days in protein-poor medium CK4 or CK4N (basic medium: mixture of ISCOVE-Ham F12 (1:1); CK4: supplementend with human albumin 50 mg/l; human transferrin, 30% saturated by addition of FeCl3, 1 mg/l; bovine insulin 3 mg/l; linoleic acid 1 mg/l; putrescine 10 µM; ethanolamine 20 µM; CK4N: same composition plus ribonucleotides: adenosine 100 mg/l, cytidine 100 mg/l, guanosine 100 mg/l, uridine 100 mg/l). This yield of secretion can be multiplied 3 times if medium is renewed every 3 days.

* Cells immortalized in vitro with EBV (line INTS-F5)

The same experiment as described before with CCL156 was reproduced with the F5 cell line which was previously used for the production of monoclonal antibodies (Goosens et al. J. Immunol. Methods 1987, 101, 193). They were transfected with the vector pTS39-Epo. Epo dosages were performed at various times after transfection and were found positive: 29 U Epo/ml/10$^6$ cells were obtained after 21 days of selection.

2.6 Measurement of biological and immunoloaical activity of RH-Epo.

Culture of foetal liver erythroblastes

The Epo activity was measured in vitro by the incorporation of $^{59}$Fe into mouse foetal liver erythroblastes (collected from 13 days pregnant females) cultivated for 26 hours, as described by Stephenson et al (Endocrinology 88, 1519, 1971).

Cells were mechanically dissociated and resuspended at the concentration of 1.6 10$^6$ cells/ml of RPMI 1640 medium (Tambourin et al. Biomedicine 19, 112, 1983; Goldwasser et al. Endocrinology 97, 315, 1975) containing 7% foetal calf serum, albumin 85 µM and human transferrine 0.4 µM.

In certain conditions serum-free medium was used which contains natural phospholipids (soja, egg lecithine) purified from natural sources or synthetic (32 10$^{-3}$M) and cholesterol (1.6 10$^{31\ 3}$M), solubilized in chloroform which is evaporated under nitrogen stream afterward. Lipids were solubilized in an albumin solution (1 mg/ml in RPMI) by ultrasonication in chilling ice bath (Boffa et coll. Exp. Hematol. 10, 675, 1982).

The cell suspension was aliquoted as 200 µl samples and distributed in the wells of culture microplates Nunclon®. After 21 hour incubation at 37° C. under 0.7% CO$_2$, $^{59}$Fe-transferrine was added in the wells; the microplates were shaken and further incubated for 5 hours.

Each sample was measured at 3 or 4 different protein concentrations and each activity was measured 4 times. The rate of incorporation of $^{59}$Fe on the methylacetone extracted heme or in the cells was measured as a function of the logarithm of the amount of sample; the results are expressed as milliunits/ml or mg proteins.

The standard is recombinant human Epo with a titer of 100000 U/mg. Its specific activity is determined by comparison with the human Epo second international standard (Annable et al, Bull. Wld. Hlth. Org. 47, 99, 1972).

Culture of bone marrow stem cells or of peripheral blood cells.

The influence of RH-Epo on cell maturation of BFUe and CFUe was determined in cultures of cell precursors of erythrocytes on methylcellulose-IMDM serum-free medium (Cormier et al, Cell Differentiation, 17, 261, 1985). RH-Epo like urinary Epo promotes the differentiation and maturation of mouse bone marrow derived or human peripheral blood derived BFUe. The dose relationship of RH-Epo on the CFUe development was compared with that of natural Epo.

Radio-immuno- dosage

Radio-immuno- dosage of RH-Epo was performed on cell supernatants following 2 methods: 1—by double antibody precipitation in liquid phase: a monospecific anti-human urinary Epo rabbit immune serum (Terry Fox Lab. Vancouver) was incubated with a human Epo standard or with a test-sample for 16 hours at 4° C. 2000 cpm$^{125}$I-RH-Epo (Amersham) were then added and the mixtures were incubated for 2 hours at 4° C. The immune serum dilution was chosen to provide an adsorbed radioactivity of 20–30%. The final dilution of the immune serum is between $10^{-4}$ and $10^{31}$ [5]. After 2 hours incubation period at 20° C. in the presence of anti-rabbit Fc goat immunoglobulins, radioactivity was measured in the pellet. 2—by double antibody precipitation in solid phase on TACHISORB®: Reactants were distributed at once on microtitration plates, DYNATECH® with 96 wells, in a final volume of 220 µl. After a 2 hour incubation period under horizontal rotative shaking at room temperature, harvesting was performed on glass hollow fiber filter on a SKATRON® apparatus. Reactants include 100 µl Epo (standard or test sample), 10 µl anti-Epo immune serum, 10 µl $^{125}$I-RH-Epo and 100 µl TACHISORB®. Once the samples were adsorbed in the glass hollow fibers they were transferred into polystyrene tubes in order to measure their radioactivity.

The sensitivity of the method is comprised between 1 and 100 mU.

The activity measured with supernatants of transformed cells reaches 800 U/ml whereas supernatants of cells transformed with anti-sense vectors do not show any activity. One observes an excellent correlation between in vitro biological activity and radioimmuno- dosage.

2.7. Detection and measurement of the in vivo biological activity of RH-Epo

The in vivo activity of the Epo collected from the supernatants of cultures of transformed lymphoblastoid cells were injected into mice artificially rendered polyglobulic in order to inhibit their endogenous Epo synthesis (Jacobson, et al Proc. SOc. Exp. Biol. Med. 94,243, 1957). The Epo from lymphoblastoid cells shows a high biological activity, comparable to that of RH-Epo produced in CHO cells (patent of Kirin-Amgen-EP 0 148 605).

The results are also in accordance with the in vitro biological dosages as performed in comparison with the international standard of human urinary Epo.

EXAMPLE 3
Epo purification and concentration methods from culture supernatant of transformed lymphoblastoid cells.
3. a First method The supernatant of a cell culture in protein-poor medium (CK4) was concentrated by ultrafiltration on PM10 membrane (AMICON®) or by tangential filtration on MINITAN® with PLGC membrane followed by washing with a solution of glucose 12.5 mM, galactose 12.5 mM, PEG 6000 0.1 mg/ml, β-mercaptoethanol $10^{-4}$M, until the filtrate reaches a resistivity higher than 5000 Ohms.

The concentrate was lyophilized and submitted to chromatography on ULTROGEL® AcA44 in a buffer containing calcium acetate 10 mM, NaCl 100 mM, phenol 5.6 $10^{-4}$M, glucose 12.5 mM, galactose 12.5 mM, PEG 6000 0.1 mg/ml, at pH 6.8. The active fractions were concentrated by ultrafiltration and lyophilized. The product was further purified by HPLC on a DEAE-TSK 545 column in a buffer containing acetate 0.048 mM, CaCl$_2$ 3 mM, glucose 12.5 mM, galactose 12.5 mM, PEG-6000 0.1 mg/ml, β-mercaptoethanol $10^{-4}$M, and eluted with a discontinuous gradient of NaCl. One recovers about 75% of the activity. After dialysis and concentration of the product, it was further subjected to chromatography on COM-AFFIGEL-BLUE in a 10 mM phosphate buffer containing NaCl 150 mM, at pH 7.2. Epo was eluted with 1.15M NaCl. The specific activity of Epo is higher than 100000 U/mg.
3. b Second Method Cell culture medium concentrated by ultrafiltration was injected on DEAE-SEPHACEL® at 4° C. in a buffer containing acetate 48 mM, CaCl$_2$ 3 mM, phenol 5.4 $10^{-4}$M, at pH 4.5. The adsorbed activity was eluted with 0.6M NaCl.

The eluate was dialyzed, concentrated and filtred on ULTROGEL® AcA44. The active fraction was detected by RIA and subjected to DEAE-HPLC in the presence of reducing agents and hexoses as stabilizers. RH-Epo eluted with pH 5.5 buffer with low NaCl molarity was further concentrated on AMICON® PM10 membrane, and injected on a column of WGA-SEPHAROSE 6MB in PBS buffer at 4° C.

It was eluted with 0.5M N-acetylglucosamine. The product was analysed by SDS-PAGE with a gradient of polyacrylamide from 4 to 30% and a component of 34 KDa was observed. This component was identified by immunoblotting with polyclonal anti-Epo immunoglobulins and with monoclonal anti RH-Epo antibodies. A minor component migrating at 42 KDa was observed with some preparations. This component was not detected by immunoblotting with anti-Epo polyclonal serum. This result is confirmed by radioimmuno- detection and by studies on mouse foetal kidney erythroblastes.

A-further purification step can be performed when appropriate, either on CM-AFFIGELL BLUE® or on HA-ULTROGEL® or by HPLC in SDS 0.1% medium. The apparent molecular weight of RH-Epo as determined on polyacrylamide-SDS gel is 34 KDa.

Its specific activity is higher than 120000 U/mg as measured in erythroblast cultures and in RIA, with a 20–30% efficiency of recovery.

3. c Third method: immunopurification of RH-Epo C-1
Preparation of the immunosorbent RH-Epo from cell supernatants was purified as described before in the second method. Its specific activity as determined by RIA and by its activity on erythroblast culture was 130000 IU. Lyophilized RH-Epo was re-solubilized in the presence of 0.05% SDS and used to immunize Balb/c mice.

Each mouse was injected intraperitoneally at 15 day intervals with the following doses: 90, 45 and 10 or 35 mg for the last injection.

The fusions were performed 5 days after the last injection. 30 to 90% of the fusion wells were tested. Antibodies were detected in the supernatant by their capacity to bind $^{125}$I-RH-Epo. The radiolabelled complexes were detected with a goat antibody, anti-mouse IgG, covalently linked on staphylococcal protein A. The complexes were collected and their radioactivity was measured.

From the 10$^{th}$ fusion, 3 hybridomes were found positive and have been cloned. The serum of the mouse from which the splenocytes were derived gave an immunological reaction of 65% at the 1/3000 dilution. One monoclonal anti-Epo antibody, of the IgG class was obtained and referenced as: Ep10-141A26. Its fixing capacity is between 50 and 60%. The clone which produces this antibody remained stable after multiple sub-cloning.

Its multiplication was performed in culture and in ascite and it gave rise to a volume sufficient to purify several milligrams of antibody. The antibody purification was performed by adsorption on protein G-SEPHAROSE, the ascite fluid being buffered with 0.1M phosphate at pH 7.5; the adsorbed material was washed at pH 6.5 and eluted with a glycine-HCl 0.1M buffer at pH 2.8. Batches of 30 mg of Ep10-141 A26 purified antibody were obtained and linked on SEPHAROSE 4B (8ml of gel) activated with cyanogen bromide. The resulting column is able to adsorb about 5–6 mg of RH-Epo.

Preliminary tests have shown that Epo is adsorbed on the antibody at a near-neutral pH. Its elution was tested at various pH: 6.5, 4.5, 2.8, 2.2; it occurs mainly from pH 4.5 till 2.8.

The immunosorbent is preserved in phosphate buffer at pH 7.5 in the presence of THYMIROSAL 0.02%, at 4° C. The column may be reused for numerous cycles.

C-2 Epo purification

Purification is performed in 2 steps

First step:

The lymphoblastoid cell culture supernatant was ultrafiltred to a protein concentration of 3–4 mg/ml, dialyzed and equilibrated at pH 4.5 with acetic acid and to 1000 Ohms with water.

A precipitate was centrifuged and the supernatant was injected on a DEAE-SEPHACEL® column equilibrated with 0.04M acetate buffer containing 0.0025M $CaCl_2$ and 5.4 $10^{-4}$M phenol, in a ratio of 0.1 (expressed as volume of exchanger, in ml/ proteins injected, in mg).

The active fraction was eluted by addition of 0.6M NaCl in the buffer and represents 15–20% of the total amount of proteins injected on the column. The eluate was equilibrated at pH 7 and dialyzed until a resistivity of 80–100 Ohms was reached.

Second step

This step was performed on the immunosorbent as described before.

The eluate of the first step DEAE-SEPHACEL was injected on the immunosorbent column in 0.1M phosphate buffer at pH 4.5, at 4° C., at a flow rate of 6–7 ml/hour.

Washing was performed with the same buffer at pH 6.5. Epo was further eluted with a buffer containing 0.1M glycine-HCl, at pH 2.2, at room temperature, at a flow rate of 50 ml/hour.

The eluate was equilibrated with 1M TRIS buffer at pH 7.5.

The efficiency of recovery of Epo activity is between 50 and 60% of the active Epo in the starting material.

C-3- Characterization of the immunopurified RH-Epo produced by the lympohoblastoid cells The homogeneity of RH-Epo preparations was evaluated by densitometry after SDS-PAGE. Epo was found more than 98% homogenous and its apparent molecular weight was determined as 34000 daltons.

Its electrophoretic mobility is identical to that of Epo produced in CHO cells and of commercial standard $^{125}$I-Epo (Amersham). Its isoelectric point is between 3.5 and 4. Its specific activity is higher than that of urinary Epo and is about 200000 U/mg.

EXAMPLE 4

Use of the integrative vector plasmid to produce human Interleukin-3 in lymphoblastoid cells.

The following 30-mer oligonucleotide, complementary to the reverse of a sequence of IL-3 5' TAA GTG TGT TAT AAT TTC ATC GAT CAT GTT 3' (SEQ ID NO:6) was used as a probe to screen a genomic DNA library of human leukocytes and a cDNA library of human foetal kidney. The synthetic probe corresponds to the sequence which begins at base n° 110 downstream from the start-ATG of the IL-3 coding sequence.

Several clones were isolated and the presence of the gene was confirmed by restriction analysis. Phages shown to contain the gene were sub-cloned in pUC18 as an AccI fragment of 5.4 Kb. Before the insertion into the expression cassette, the promotor and 3' untranslanted sequences were removed. The coding sequence was amplified by PCR with the following 2 synthetic oligonucleotides INTS16: 5' GATCCAAACATGAGCCGCCT 3' (SEQ ID NO:7) which corresponds to the position -9 from the ATG INTS17: 5' ATGTCCCGAGGCGCTGTGGT 3' (SEQ ID NO:8) which corresponds to the position 52 downstream from the stop codon, and using the previously characterized genomic sequences cloned in pUC18 as templates.

The product of the amplification of a 2140 bp fragment was sub-cloned in the SmaI site of pUC18 and partially sequenced in order to confirm the integrity of the IL-3 gene (according to Yang et Clark, in "Developmental Control of globin gene expression" A.R. LISS P.3–11 1987).

The resulting well controlled coding sequence was inserted in the expression cassette of the vector plasmid described in example 1. A cell clone which gave a strongly positive expression was selected and multiplied.

Biologically active interleukin-3 was found to be secreted in the cell culture medium.

EXAMPLE 5

Use of the integrative vector plasmid to produce the human GM-CSF in lymphoblastoid cells.

The following 30-mer oligonucleotide, which is complementary to the reverse of a GM-CSF sequence 5' TTG CTC TAA GCA CTT GAG CAG GAA GCT CTG 3' (SEQ ID NO:9) was used as a probe to screen a genomic DNA library of human leukocytes and a cDNA library of human foetal kidney. The synthetic probe corresponds to the base n° 157 downstream from the start ATG of the CM-CSF coding sequence.

Several clones were selected and the presence of the gene was confirmed by restriction analysis. Phages shown to contain the gene were sub-cloned in pUC18 as a HindIII-Eco RI fragment of 3.2Kb.

Before the insertion into the expression cassette, the promotor and 3' untranslated sequences were removed. The coding sequence was amplified by PCR with the following 2 synthetic oligonucleotides: INTS 19: 5' CACA-GAGAGAAAGGCTAAAG 3' (SEQ ID NO:10) which corresponds to the position -31 from the ATG, INTS 18: 5' ATTCCCATTCTTCTGCCATG 3' (SEQ ID NO:11) which corresponds to the position 177 downstream from the stop codon, and using the previously characterized genomic sequences cloned in pUC18 as templates.

The product of the amplification of a 2240 bp fragment was sub-cloned in the SmaI site of pUC18 and partially sequenced in order to confirm the integrity of the GM-CSF gene (according to Miyatake et al. EMBO J.4, 2561, 1985).

The resulting well controlled coding sequence was inserted in the expression cassette of the vector plasmid described in example 1. A cell clone which gave a strongly positive expression was selected and multiplied.

Biologically active GM-CSF was found to be secreted in the cell culture medium.

---

We claim:

1. A plasmid vector for producing heterologous proteins designed for transforming non-tumorigenic lymphoblastoid cells, immortalized by Epstein Barr virus, which comprises the bacterial DNA elements required for its amplification together with the following DNA fragments:

one or more DNA elements which constitute an expression cassette for insertion of a heterologous DNA in the human lymphoblastoid cells, an Adenovirus 5 derived DNA sequence encoding virus associated I and virus associated II (VA I and VA II) RNA aimed at optimizing messenger RNA translation, a gene which is a selective marker in eukaryotic cells, and DNA segments which promote plasmid DNA integration into the cell chromosome DNA.

2. The plasmid vector according to claim 1, wherein the DNA elements which form an expression cassette integrated into said vector comprise:

a) a transcription activator sequence derived from an Adenovirus, b) a promotor and a leader sequence derived from an Adenovirus, c) a synthetic oligonucleotide including restriction sites aimed at integrating the DNA coding sequence of the heterologous protein, and d) a polyadenylation signal derived from SV40virus.

3. The plasmid vector according to claim 1, wherein the expression cassette comprises:

as the element a), the transcription activator sequence of the E1A gene of human Adenovirus 5, as the element b), the major late promotor of Adenovirus 2 coupled with the tripartite leader sequence of the same Adenovirus 2, and as the element c), a sequence designed to provide rare restriction sites in order to facilitate the integration of the heterologous sequence.

4. The plasmid vector according to claim 1, wherein the gene engineered to be efficient as a selective marker is selected from the group consisting of:

the E.coli DNA coding for xanthine-guanine-phosphoryl-transferase (XGPRT) inserted under the control of Herpes simplex virus 1 thymidine kinase (Tk) gene promoter and maturation signals, the mouse dihydrofolate reductase (DHFR) CDNA, and a combination of both genes, inserted at different locations in the vector plasmid.

5. The plasmid vector according to claim 1, wherein the DNA segments selected for their property to promote said plasmid DNA integration comprise a fragment of mouse mitochondrial DNA.

6. The plasmid vector according to claim 1, wherein the heterologous DNA inserted in the expression cassette is chosen among the coding sequences of useful proteins which are hard to purify from natural sources.

7. The plasmid vector according to claim 1, wherein the heterologous DNA inserted in the expression cassette is the coding sequence of erythropoietin or a protein having erythropoietin activity.

8. The plasmid vector according to claim 1, wherein the heterologous DNA inserted in the expression cassette is the coding sequence of interleukin-3 or a protein having interleukin-3 activity.

9. The plasmid vector according to claim 1, wherein the heterologous DNA inserted in the expression cassette is the coding sequence of granulocyte macrophage colony-stimulating factor (GM-CSF).

10. Human lymphoblastoid cell lines immortalized by EBV which are stably transformed by the vector according to claim 1 and screened for their high level of secretion of the heterologous protein.

11. A human lymphoblastoid cell line stably transformed by the vector according to claim 1 for which the starting cell line to be transformed by the vector plasmid is the ATCC-CCL 156 RPMI 1788 cell line.

12. A human lymphoblastoid cell line stably transformed by the vector according to claim 1 for which the starting cell line to be transformed by the vector plasmid is a cell line derived from B lymphocytes of a health donor and immortalized by EBV.

13. A method for producing, on an industrial scale, heterologous proteins encoded by a DNA fragment inserted into a genetically engineered vector plasmid, of the integrative type according to claim 1, bearing an expression cassette comprising all the elements allowing the expression of said heterologous proteins in said lymphoblastoid cells once said expression cassette is integrated into the cell chromosome DNA, the method comprising:

obtaining human lymphoblastoid cell lines which have been immortalized in vitro by Epstein-Barr virus (EBV) and selected for their absence of tumoral or tumorigenic character.

14. The plasmid vector according to claim 2, wherein the element c) sequence is selected from the group consisting of Not I, Bst EtII, Bgl II and MLuI.

* * * * *